United States Patent [19]
LaGrange et al.

[11] Patent Number: 5,478,359
[45] Date of Patent: Dec. 26, 1995

[54] PROCESS FOR DYEING KERATINOUS FIBERS AND COMPOSITIONS CONTAINING SULFUR-CONTAINING META-AMINOPHENSES

[75] Inventors: Alain LaGrange, Coupvray; Alain Genet, Aulnay-sous-Bois; Alex Junino, Livry-Gargan, all of France

[73] Assignee: L'Oreal, Paris, France

[21] Appl. No.: 162,118

[22] PCT Filed: Jun. 10, 1992

[86] PCT No.: PCT/FR92/00524

§ 371 Date: Dec. 13, 1993

§ 102(e) Date: Dec. 13, 1993

[87] PCT Pub. No.: WO92/22525

PCT Pub. Date: Dec. 23, 1992

[30] Foreign Application Priority Data

Jun. 13, 1991 [FR] France ................................ 91 07248

[51] Int. Cl.⁶ .................................................. A61K 7/13
[52] U.S. Cl. ...................... 8/412; 8/406; 8/407; 8/408; 8/421; 8/587
[58] Field of Search ................... 8/405, 406, 407, 8/408, 412, 421, 587; 564/440, 443, 448

[56] References Cited

U.S. PATENT DOCUMENTS 3,655,773  4/1972  Reifschneider ................ 564/440
3,775,485  11/1973  Pilgram ........................... 564/440
4,006,186  2/1977  Engels ............................. 564/440

FOREIGN PATENT DOCUMENTS 1061331  4/1954  France .
0301701  9/1954  Switzerland .

Primary Examiner—Paul Lieberman
Assistant Examiner—Caroline L. Dusheck
Attorney, Agent, or Firm—Jacobson, Price, Holman & Stern

[57] ABSTRACT

Composition and process for dyeing keratinous fibers using sulphurous metaaminophenols of formula (I):

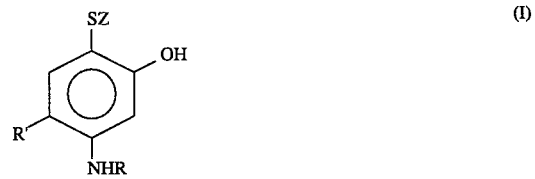

in which Z is a $C_1$–$C_{18}$ alkyl radical, an aryl radical, an aralkyl in which the alkyl radical has from 1 to 5 carbon atoms, a $C_2$–$C_6$ monohydroxyalkyl radical, a $C_2$–$C_6$ polyhydroxyalkyl radical, an aminoalkyl radical of formula (I')

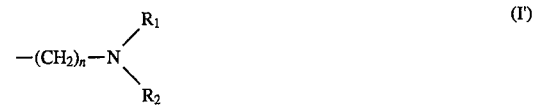

in which n is an integer of between 1 and 6 inclusive, $R_1$ and $R_2$, which may be the same or different, are a hydrogen atom or a $C_1$–$C_4$ alkyl, a $C_1$–$C_4$ hydroxyalkyl, a $C_2$–$C_6$ acyl radical; R is a hydrogen atom, a $C_1$–$C_6$ alkyl radical, a $C_1$–$C_6$ monohydroxyalkyl or a $C_2$–$C_6$ polyhydroxyalkyl radical, a $C_1$–$C_6$ monocarbamylalkyl, a $C_1$–$C_6$ dicarbamylalkyl, a $C_1$–$C_4$ aminoalkyl, a $C_1$–$C_6$ acyl, a $C_2$–$C_6$ carbalkoxy, a carbamyl or a carbamyl $C_1$–$C_6$ monoalkyl, R' is a hydrogen atom, a $C_1$–$C_4$ alkyl radical, a $C_1$–$C_4$ thioalkyl or a $C_1$–$C_4$ alkoxy, as well as the corresponding acid salts of said sulphurous metaaminophenols.

21 Claims, No Drawings

PROCESS FOR DYEING KERATINOUS FIBERS AND COMPOSITIONS CONTAINING SULFUR-CONTAINING META-AMINOPHENSES

The present invention relates to the use of sulfur-containing meta-aminophenols for the dyeing of keratinous fibers, especially human hair, to dyeing compositions, to dyeing processes and to new compounds of the sulfur-containing meta-aminophenol family.

The compounds used for the dyeing of keratinous fibers, especially human hair, according to the invention, correspond to the formula:

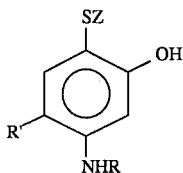
(I)

in which Z represents a $C_1$–$C_{18}$ alkyl radical, an aryl radical, an aralkyl radical in which the alkyl radical contains 1 to 6 carbon atoms, a monohydroxyalkyl radical containing 1 to 6 carbon atoms or a $C_2$–$C_6$ polyhydroxyalkyl radical, an aminoalkyl radical of formula

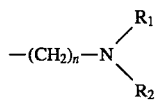
(I')

in which n is an integer between 1 and 6 inclusive, $R_1$ and $R_2$, which may be identical or different, represent a hydrogen atom or a $C_1$–$C_4$-alkyl, $C_1$–$C_4$ hydroxyalkyl, $C_2$–$C_6$ acyl radical;

R represents a hydrogen atom, a $C_1$–$C_6$ alkyl radical, a $C_1$–$C_6$ monohydroxyalkyl, $C_2$–$C_6$ polyhydroxyalkyl, monocarbamyl ($C_1$–$C_6$ alkyl), dicarbamyl ($C_1$–$C_6$ alkyl), $C_1$–$C_6$ aminoalkyl, $C_1$–$C_6$ acyl, $C_2$–$C_6$ carbalkoxy, carbamyl or mono ($C_1$–$C_6$ alkyl)carbamyl radical, R' represents a hydrogen atom, a $C_1$–$C_4$ alkyl, $C_1$–$C_4$ thioalkyl or $C_1$–$C_4$ alkoxy radical, as well as the corresponding salts with an acid to the compounds of formula (I) [sic].

Among preferred meanings of the radical Z, there may be mentioned, for the meaning $C_1$–$C_{18}$ alkyl, methyl, ethyl, propyl, butyl radicals; the aralkyl radical denotes benzyl; the aryl radical denotes phenyl, the mono- or polyhydroxyalkyl radical preferably denotes —$CH_2$—$CH_2OH$, —$CH_2CHOH$—$CH_2$—OH, —$CH_2CHOH$—$CH_3$, aminoalkyl preferably denotes —$CH_2$—$CH_2$—$NH_2$,

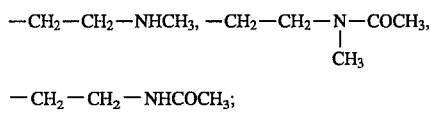

—$CH_2$—$CH_2$—$NHCOCH_3$;

when R represents acyl, it preferably denotes formyl, acetyl and propionyl.

The salts with an acid are preferably chosen from hydrochlorides, sulfates or hydrobromides.

Especially preferred compounds falling within the definition of the formula (I) are chosen from:
—2-methylthio-5-aminophenol,
—2-ethylthio-5-aminophenol,
—2-butylthio-5-aminophenol,
—2-benzylthio-5-aminophenol,
—2-(β-hydroxyethylthio)-5-aminophenol,
—2-(β-acetylaminoethylthio)-5-aminophenol,
—2-methylthio-5-ureidophenol,
—2-methylthio-5-acetylaminophenol,
—2-methylthio-5-(carbethoxyamino)phenol,
—2,4-bis(methylthio)-5-aminophenol,
—2-(4'-amino-2'-hydroxyphenyl)thio-5-aminophenol,
—2-(4'-nitrophenyl)thio-5-aminophenol,
—2-(2'-aminophenyl)thio-5-aminophenol.

The compounds corresponding to the formula (I) are more especially used as couplers in the presence of of para or ortho oxidation dye precursors which are known per se, enabling keratinous fibers, and especially hair, to be dyed according to a process employing an oxidative condensation reaction of the precursors and of the coupler or couplers present.

Among the compounds used according to the invention, there are new compounds which constitute another subject of the invention.

These compounds correspond to the formula (IA):

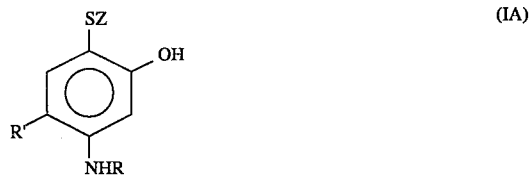
(IA)

in which Z represents a $C_1$–$C_{18}$ alkyl radical, an aralkyl radical in which the alkyl radical contains 1 to 6 carbon atoms, a $C_1$–$C_6$ monohydroxyalkyl radical, a $C_2$–$C_6$ polyhydroxyalkyl radical, an aminoalkyl radical of formula:

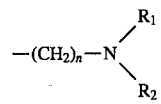

in which n is an integer between 1 and 6 inclusive, $R_1$ and $R_2$, which may be identical or different, represent a hydrogen atom or a $C_1$–$C_4$-alkyl, $C_1$–$C_4$ hydroxyalkyl, $C_2$–$C_6$ acyl radical;

R represents a hydrogen atom, a $C_1$–$C_6$ alkyl radical, a $C_1$–$C_6$ monohydroxyalkyl, $C_2$–$C_6$ polyhydroxyalkyl, monocarbamyl ($C_1$–$C_6$ alkyl), dicarbamyl ($C_1$–$C_6$ alkyl), $C_1$–$C_6$ aminoalkyl, $C_1$–$C_6$ acyl, $C_2$–$C_6$ carbalkoxy, carbamyl or mono ($C_1$–$C_6$ alkyl)carbamyl radical, R' represents a hydrogen atom, a $C_1$–$C_4$ alkyl, $C_1$–$C_4$ thioalkyl or $C_1$–$C_4$ alkoxy radical, with the proviso that, when R and R' denote a hydrogen atom, Z cannot denote butyl, β, γ, -dihydroxypropyl and diethylaminoethyl radicals, as well as the corresponding salts with an acid.

The compounds of formula (I) or their salts may be prepared according to a process that consists, in a first step, in reacting 3,4-methylenedioxy-1-nitrobenzene, optionally substituted at position 2 with an alkyl, thioalkyl or alkoxy group, in the presence of a base such as potassium hydroxide, potassium carbonate, with a thiol of formula (II):

(II)

in which Z represents either a $C_1$–$C_{18}$ alkyl group, an aralkyl group in which the alkyl radical is a $C_1$–$C_6$ radical, or a monohydroxyalkyl group having 1 to 6 carbon atoms [lacuna] $C_2$–$C_6$ polyhydroxyalkyl group, a group of formula:

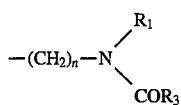

5 where $R_1$ and n have the meanings stated above and where $R_3$ represents a hydrogen atom or an alkyl radical having 1 to 3 carbon atoms; in a second step, the $NO_2$ group of the compound of the formula (III)

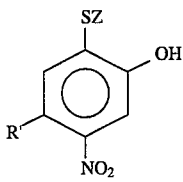

(III)

where Z has the same meaning as in the formula (I) and R' represents hydrogen, alkyl, alkoxy or thioalkyl, obtained above, is reduced to prepare a compound corresponding to the formula (IV:)

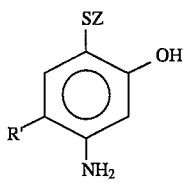

(IV)

in which Z and R' have the meaning stated above; where appropriate, in a third step, and depending on the compound of formula (I) which is desired, the compound of formula (IV) is converted, either by acid hydrolysis, in particular using hydrochloric acid when Z comprises an acylated amine group, or by substitution of the extranuclear amine when Z contains an amine group, or by monosubstitution of the aromatic amine.

In the special case where Z represents an alkyl and R' thioalkyl, the compounds of formula (I) may be prepared by reacting, in the first place, an excess of alkali metal thioalkylate ZSM, where Z=alkyl and M=alkali metal, with 3,4-methylenedioxy-6-(trifluoroethyl)nitrobenzene to obtain a compound of formula (IIIA):

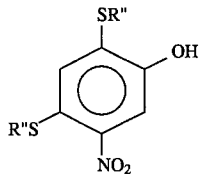

(IIIA)

where R"=alkyl, which, in a second step, is subjected to a reduction.

The reduction of the nitro group of the compounds of formulae (III) and (IIIA) is preferably performed using iron in an acetic medium, or else with cyclohexene in the presence of a palladium/charcoal catalyst, or by any other standard reduction process.

When Z contains an acylated amine group and the compound of formula (IV) is subjected to an acid hydrolysis, a compound of formula (V):

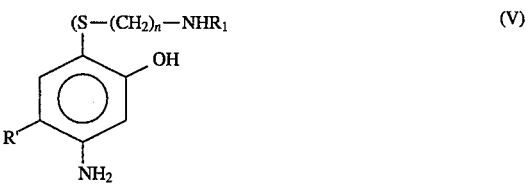

(V)

in which n, $R_1$ and R' have the meanings as stated above, is obtained.

The compounds of formula [sic] (IV) and (V) and their derivatives obtained from them by substitution of the aromatic or extranuclear amine are collectively covered by the compounds of formula (I).

For the substitution of the aromatic or extranuclear amines, it is possible to react, for example, ethyl bromide, glycol bromohydrin, ethyl chloroformate, β-chloroacetamide, acetic anhydride.

The use of the compounds of formula (I) for the dyeing of keratinous fibers is accomplished, more especially, using so-called oxidation dyeing compositions.

The dyeing composition which constitutes another subject of the invention is essentially characterized in that it contains, in a medium suitable for the dyeing of keratinous fibers, which is cosmetically acceptable when the fibers are hair, a para or ortho type oxidation dye precursor and at least one sulfur-containing meta-aminophenol of formula (I) defined above.

The para or ortho type dye precursors used according to the invention are compounds which are not dyes in themselves, but which form dyes by a process of oxidative condensation, either with themselves or in the presence of a coupler or modifier.

These para or ortho type oxidation dye precursors are benzenoid or heterocyclic compounds which contain two amino groups or alternatively an amino group and a hydroxyl group in the para or ortho position with respect to one another.

The para or ortho type oxidation dye precursors may be chosen from para-phenylenediamines, paraaminophenols, heterocyclic para precursors derived from pyridine or pyrimidine, such as 2,5-diaminopyridine, 2-hydroxy-5-aminopyridine, 2,4,5,6-tetraaminopyrimidine, 4,5-diamino-1-methylpyrazole, 2-dimethylamino-4,5,6-triaminopyrimidine, ortho-aminophenols and so-called "double" bases.

As para-phenylenediamines, there may be mentioned, more especially, the compounds corresponding to the formula (VI):

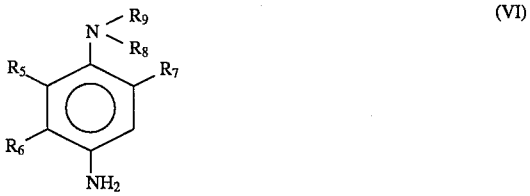

(VI)

in which:

$R_5$, $R_6$, $R_7$, which may be identical or different, represent a hydrogen or halogen atom, an alkyl radical, an alkoxy radical, a carboxyl, sulfo, $C_1$–$C_4$ hydroxyalkyl radical;

$R_8$ and $R_9$, which may be identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, morpholinoalkyl radical, a phenyl radical optionally substituted at the para position with an amino group; or alternatively $R_8$ and $R_9$, together with the nitrogen atom to which they are linked, form a piperidino or morpholino heterocycle, with the proviso that $R_5$ or $R_7$ represent [sic] a hydrogen atom when $R_8$ and $R_9$ do not represent hydrogen, as well as the salts of its [sic] compounds.

The alkyl or alkoxy radicals preferably denote a group having 1 to 4 carbon atoms, and in particular methyl, ethyl, propyl, methoxy, ethoxy.

Among the compounds of formula (VI), there may be mentioned para-phenylenediamine, p-toluylenediamine, methoxy-para-phenylenediamine, chloro-para-phenylenediamine, 2,3-dimethyl-para-phenylenediamine, 2,6-dimethyl-para-phenylenediamine, 2,6-diethyl-paraphenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine [lacuna] N,N-dipropyl-para-phenylenediamine, 3-methyl-4-amino-N,N-diethylaniline, N,N-di(β-hydroxyethyl)-para-phenylene-diamine, 3-methyl-4-amino-N,N-di(β-hydroxyethyl)aniline, 3-chloro-4-amino-N,N-di(β-hydroxyethyl)aniline, 4-amino-N,N-(ethylcarbamylmethyl)aniline, 3-methyl-4-amino-N, N(ethyl,carbamylmethyl)aniline, 4-amino-N,N-(ethyl,β-piperidinoethyl)aniline, 3-methyl-4-amino-N,N-(ethyl, β-piperidinoethyl)aniline, 4-amino-N,N-(ethyl, β-morpholinoethyl)aniline, 3-methyl-4-amino-N,N-(ethyl,β-morpholinoethyl)aniline, 4-amino-N,N-(ethyl, β-acetylaminoethyl)aniline, 4-amino-N-(β-methoxyethyl)aniline, 3-methyl-4-amino-N,N-(ethyl,β-acetylaminoethyl)aniline, 4-amino-N, N-(ethyl,β-mesylaminoethyl)aniline, 3-methyl-4-amino-N, N-(ethyl,β-mesylaminoethyl)aniline, 4-amino-N,N-(ethyl, β-sulfoethyl)aniline, 3-methyl-4-amino-N,N-(ethyl,β-sulfoethyl)aniline, N-[(4'-amino)phenyl]morpholine [sic], N-[(4'-amino)phenyl]piperidine [sic], 2-hydroxyethyl-para-phenylenediamine, fluoro-para-phenylenediamine, carboxy-para-phenylenediamine, sulfo-paraphenylenediamine, 2-isopropyl-para-phenylenediamine, 2-n-propyl-para-phenylenediamine, hydroxy-2-n-propyl-paraphenylenediamine, 2-hydroxymethyl-para-phenylenediamine, N,N-dimethyl-3-methyl-para-phenylenediamine, N,N-(ethyl,α-hydroxyethyl)-para-phenylenediamine, N-(di-hydroxypropyl)-para-phenylenediamine, N-4'-aminophenyl-para-phenylenediamine [sic], N-phenyl-para-phenylenediamine.

These para type oxidation dye precursors may be introduced into the dyeing composition either in free base form, or in the form of salts such as hydrochloride, hydrobromide or sulfate.

Among p-aminophenols, there may be mentioned p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-(β-hydroxyethyl)-4-aminophenol, 2-methoxy-4-aminophenol, 3-methoxy-4-aminophenol, 3-(β-hydroxyethoxy)-4-aminophenol, 2-methoxy-methyl-para-aminophenol, 2-aminomethyl-4-aminophenol, 2-β-hydroxyethylaminomethyl-4-aminophenol [sic], 2-ethoxymethyl-p-aminophenol, 2-(β-hydroxyethoxy)methyl-p-aminophenol.

The so-called double bases are bis(phenyl)alkylenediamines corresponding to the formula:

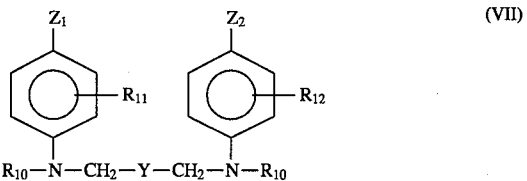

(VII)

in which:

$Z_1$ and $Z_2$, which may be identical or different, represent hydroxyl groups or groups $NHR_{13}$, where $R_{13}$ denotes a hydrogen atom or a lower alkyl radical;

$R_{11}$ and $R_{12}$, which may be identical or different, represent either hydrogen atoms or halogen atoms or alternatively alkyl groups;

$R_{10}$ represents a hydrogen atom, an alkyl or hydroxyalkyl group or an aminoalkyl group in which the amino residue may be substituted;

Y represents a radical selected from the group consisting of the following radicals:

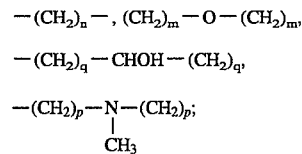

n is an integer between 0 and 8 and m, q and p are integers between 0 and 4. It being possible for this base also to take the form of its addition salts with acids.

The alkyl or alkoxy radicals mentioned above preferably denote a group having 1 to 4 carbon atoms, and in particular methyl, ethyl, propyl, methoxy, ethoxy.

Among the compounds of formula (VIII [sic]), there may be mentioned N,N'-bis(β-hydroxyethyl)-N,N'-bis(4'-aminophenyl)-1,3-diamino-2-propanol, N,N'-bis(β-hydroxyethyl)-N,N' -bis(4'-aminophenyl)ethylenediamine, N,N'-bis(4-aminophenyl) tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine.

Among ortho-aminophenols, there may be mentioned 1-amino-2-hydrobenzene [sic], 6-methyl-1-hydroxy-2-aminobenzene, 4-methyl-1-amino-2-hydroxybenzene, 4-acetylamino-1-amino-2-hydroxy benzene.

The dyeing compositions may also contain, in addition to the coupler corresponding to the formula (I) defined above, other couplers which are known per se, such as meta-diphenols, meta-aminophenols, meta-phenylenediamines, meta-acylaminophenols, meta-ureidophenols, meta-carbalkoxyaminophenols, α-naphthol, indole derivatives, couplers possessing an active methylene group, such as β-keto compounds, pyrazolones.

There may be mentioned, more especially, as an example, 2,4-dihydroxyphenoxyethanol, 2,4-dihydroxyanisole, meta-aminophenol, resorcinol monomethyl ether, resorcinol, 2-methylresorcinol, 2-methyl-5-aminophenol, 2-methyl-5-N-(β-hydroxyethyl)aminophenol, 2-methyl-5-N-(β -mesylaminoethyl)aminophenol, 2,6-dimethyl-3-aminophenol, 6-hydroxybenzomorpholine, 2,4-diaminoanisole, 2,4 -diaminophenoxyethanol, 6 -aminobenzomorpholine, [2-N-(β

-hydroxyethyl) amino-4-amino]phenoxyethanol [sic], 2-amino-4-N-(β-hydroxyethyl) aminoanisole, (2)-4-diamino)phenyl [sic]β,γ-dihydroxypropyl ether, 2,4-diaminophenoxyethylamine, 1,3-dimethoxy-2,4-diaminobenzene, 1,3,5-trimethoxy-2,4-diaminobenzene, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, 6-methoxy-3-hydroxyethylaminoaniline, 1-ethoxy-2-bis-(β-hydroxyethyl)amino-4-aminobenzene, 3-diethylaminophenol, 1,3-dihydroxy-2-methylbenzene, 1-hydroxy-2,4-dichloro- 3-aminobenzene, 4,6-hydroxyethoxy-1,3-diaminobenzene, 4-methyl-6-ethoxy-1,3-diaminobenzene, 4-chloro- 6-methyl-3-aminophenol, 6-chloro-3-trifluoroethylaminophenol, and their salts.

Direct dyes such as azo, anthraquinone dyes or nitro derivatives of the benzene series may be added to these compositions, as is well known in the state of the art.

The para and/or ortho type oxidation dye precursors as well as the couplers used in the dyeing compositions according to the invention preferably represent collectively from 0.3 to 7% by weight relative to the total weight of the composition. The concentration of compounds (I) can vary between 0.05 and 3.5% by weight of the total weight of the composition.

The appropriate solvent medium for the dyeing is generally aqueous, and its pH can vary between 4 and 11.

It is adjusted to the desired value using alkalinizing agents which are well known in the state of the art, such as ammonia solution, alkali metal carbonates, alkanolamines such as mono-, di- or triethanolamine.

The dyeing compositions according to the invention also contain, in their preferred embodiment, anionic, cationic, nonionic, amphoteric surfactants or mixtures thereof. Among these surfactants, there may be mentioned alkylbenzenesulfonates, alkylnaphatalenesulfonates [sic], the sulfates, ether sulfates and sulfonates of fatty alcohols, quaternary ammonium salts such as trimethylcetylammoniumbromide, cetylpyridiniumbromide, optionally oxyethylenated fatty acid ethanolamides, polyglycerolated alcohols, polyoxyethylenated or polyglycerolated alkylphenols as well as polyoxyethylenated alkyl sulfates.

These surfactants are present in the compositions according to the invention in proportions of between 0.5 and 55% by weight, and preferably between 2 and 50% by weight, relative to the total weight of the composition.

These compositions can also contain organic solvents to solubilize compounds which might not be sufficiently soluble in water. Among these solvents, there may be mentioned, as an example, $C_1$–$C_4$ lower alkanols such as ethanol and isopropanol; glycerol; glycols or glycol ethers such as 2-butoxyethanol, ethylene glycol, propylene glycol, diethylene glycol monoethyl ether and monomethyl ether, as well as aromatic alcohols such as benzyl alcohol or phenoxyethanol, similar products and mixtures thereof.

The solvents are preferably present in proportions of between 1 and 40% by weight, and especially between 5 and 30% by weight, relative to the total weight of the composition.

The thickening agents which may be added to the compositions according to the invention may be chosen from sodium alginate, gum arabic, cellulose derivatives, heterobiopolysaccharides such as xanthan gum, optionally crosslinked acrylic acid polymers. It is also possible to use inorganic thickening agents such as bentonite. These thickening agents are preferably present in proportions of between 0.1 and 5%, and especially between 0.2 and 3%, by weight relative to the total weight of the composition.

The antioxidants which may be present in the compositions are chosen especially from sodium sulfite, thioglycolic acid, sodium bisulfite, dehydroascorbic acid, hydroquinone and homogentisic acid. These antioxidants are present in the composition in proportions of between 0.05 and 1.5% by weight relative to the total weight of the composition.

These compositions may also contain other cosmetically acceptable adjuvants such as, for example, penetrating agents, sequestering agents, perfumes, buffers and the like.

The compositions according to the invention can assume various forms, such as the form of liquids, creams, gels, or any other form suitable for carrying out a dyeing of keratinous fibers, and in particular human hair. These compositions may be packaged in aerosol cans in the presence of a propellent agent, and may form foams.

The dyeing compositions according to the invention, containing a para and/or ortho type oxidation dye precursor and a coupler of formula (I), are used according to a process that employs development with an oxidizing agent.

According to this process, the dyeing composition described above is mixed at the time of use with an oxidizing solution in a sufficient amount to be able to develop a coloration, the pH of the resulting composition being below 8, and the mixture obtained is then applied to the keratinous fibers, and especially human hair.

The pH of the composition applied to the hair preferably varies between 3.5 and 7. The oxidizing solution contains, as oxidizing agent, hydrogen peroxide, urea peroxide, persalts such as ammonium persulfate or alkali metal bromates. It is preferable to use a 20-volumes hydrogen peroxide solution.

The mixture obtained is applied to the hair and left in place for 10 to 40 minutes, and preferably 15 to 30 minutes, after which the hair is rinsed, washed with shampoo, rinsed again and dried.

The coupler of formula (I) defined above may also be employed in a multi-step process consisting, in one of the steps, in applying the oxidation dye precursor of the para and/or ortho type or mixture thereof, and in another step, in applying a dyeing composition containing the coupler of formula (I).

The oxidizing agent may be introduced immediately before application into the composition applied in the second stage, or alternatively be applied to the keratinous fibers themselves in a third stage, the exposure, drying and washing conditions being identical to those stated above.

The examples which follow are designed to illustrate the invention, no limitation thereof being, however, implied.

PREPARATION EXAMPLE 1

Synthesis of 2-methylthio-5-aminophenol

1st step: Synthesis of 2-methylthio-5-nitrophenol 167 g (1 mol) of 4-nitro-1,2-methylenedioxybenzene are added portionwise in the course of 35 minutes to a suspension, stirred at room temperature, of 100 g (1.42 mol) of sodium thiomethylate in 300 ml of N-methylpyrrolidone so as to maintain the reaction temperature at between 35° and 40° C. This heating is prolonged after the end of the addition until reaction is complete (approximately 20 minutes).

The reaction mixture is poured into 2.2 liters of ice-cold water. The solution obtained is neutralized with approximately 100 ml of glacial acetic acid.

An oil precipitates and crystallizes.

The product is drained and washed with water.

After recrystallization from 400 ml of isopropyl acetate under reflux, 148.2 g of yellow crystals are obtained, the melting point of which is 145° C.

Elemental analysis calculated for $C_7H_7NO_3S$

|  | C | H | N | O | S |
|---|---|---|---|---|---|
| Theory | 45.39 | 3.81 | 7.56 | 25.92 | 17.31 |
| Found | 45.51 | 3.79 | 7.61 | 26.18 | 17.38 |

2nd step: Synthesis of 2-methylthio-5-aminophenol.

The suspension obtained on mixing 150 ml of 96° strength ethanol, 16 ml of water, 2.3 g of ammonium chloride and 78 g of finely powdered zinc is brought to reflux. 25.1 g (0.15 mol) of 2-methylthio-5-nitrophenol are added portionwise so as to maintain the reflux without heating (exothermic reaction).

The reflux is maintained until reaction is complete (decolorization).

The mixture is filtered while hot and the zinc is washed with the minimum amount of boiling alcohol.

The filtrate is cooled in an ice bath.

The crystallized precipitate obtained is drained, washed with alcohol and dried under vacuum.

After concentration of the mother liquors, a second crop of crystals is obtained.

10.5 g of white crystals are obtained in all, the melting point of which product is 175° C.

Elemental analysis calculated for $C_7H_9NOS+¼H_2O$

|  | C | H | N | O | S |
|---|---|---|---|---|---|
| Theory | 52.64 | 5.99 | 8.77 | 12.52 | 20.08 |
| Found | 52.91 | 5.83 | 8.91 | 12.68 | 20.10 |

PREPARATION EXAMPLE 2

Synthesis of 2-ethylthio-5-aminophenol.

1st step: Synthesis of 2-ethylthio-5-nitrophenol.

Prepared according to the procedure of Example 1, 1st step, yellow crystals are obtained, the melting point of which is 93° C. (recrystallized from benzene).

Elemental analysis calculated for $C_8H_9NO_3S$

|  | C | H | N | O | S |
|---|---|---|---|---|---|
| Theory | 48.23 | 4.55 | 7.03 | 24.09 | 16.09 |
| Found | 48.12 | 4.61 | 7.18 | 23.86 | 16.32 |

2nd step: Synthesis of 2-ethylthio-5-aminophenol.

100 g of technical sodium hydrosulfite are added to a solution of 25.6 g (0.64 mol) of sodium hydroxide pellets in 320 ml of water, and the temperature is brought to 50° C.

39.8 g (0.2 mol) of 2-ethylthio-5-nitrophenol are added portionwise while the temperature is maintained at between 55° and 60° C.

At the end of the addition, 50 ml of 10N caustic soda and 20 g of sodium hydrosulfite are added to maintain alkalinity and complete the reduction.

After approximately 20 minutes at 55°–60° C., the mixture is cooled in an ice bath and neutralized with glacial acetic acid, and the precipitated solid is drained and washed with water.

This solid is dissolved in 500 ml of ethyl acetate, treated with 10 g of LECA charcoal and dried over sodium sulfate.

After filtration, the mixture is evaporated to dryness under reduced pressure and the residue is taken up in the minimum amount of dichloromethane.

The white crystals formed are drained (7 g) and recrystallized from acetonitrile; the melting point is 129° C.

Elemental analysis calculated for $C_8H_{11}NOS$

|  | C | H | N | O | S |
|---|---|---|---|---|---|
| Theory | 56.77 | 6.55 | 8.28 | 9.45 | 18.95 |
| Found | 56.88 | 6.54 | 8.26 | 9.62 | 18.76 |

PREPARATION EXAMPLE 3

Synthesis of 2-butylthio-5-aminophenol.

1st step: Synthesis of 2-butylthio-5-nitrophenol

Prepared according to the procedure of Example 1, step 1, yellow crystals are obtained, the melting point of which is 50° C. (recrystallized from cyclohexane) and the elemental analysis of which, calculated for $C_{10}H_{13}NO_3S$ ½ mol of N-methylpyrrolidone, is:

|  | C | H | N | O | S |
|---|---|---|---|---|---|
| Theory | 54.23 | 6.37 | 7.59 | 20.23 | 11.58 |
| Found | 54.86 | 6.31 | 7.77 | 20.40 | 11.04 |

2nd step: Synthesis of 2-butylthio-5-aminophenol.

Prepared according to the procedure of Example 1, step 2, white crystals are obtained, the melting point of which is 92° C. (recrystallized from 95° strength ethanol) and the elemental analysis of which, calculated for $C_{10}H_{15}NOS$, is:

|  | C | H | N | O | S |
|---|---|---|---|---|---|
| Theory | 60.88 | 7.66 | 7.10 | 8.11 | 16.25 |
| Found | 60.92 | 7.71 | 7.04 | 8.30 | 16.20 |

PREPARATION EXAMPLE 4

Synthesis of 2-benzylthio-5-aminophenol.

1st step: Synthesis of 2-benzylthio-5-nitrophenol.

A suspension of 33.4 g (0.2 mol) of 4-nitro-1,2-methylenedioxybenzene and 30.4 g of potassium carbonate in 100 ml of N-methylpyrrolidone is heated to 90° C. under nitrogen. In the course of 1 hour, a solution of 24.8 g (0.2 mol) of benzyl mercaptan in 50 ml of N-methylpyrrolidone is run in dropwise.

The reaction mixture is poured into 1 liter of ice-cold water. The slight precipitate which has crystallized is removed by filtration and the orange-colored filtrate is acidified with glacial acetic acid.

The oil thus precipitated is separated after settling has taken place and dissolved in 90 ml of isopropanol.

On addition of water, pale yellow crystals are precipitated, which are drained and recrystallized in 40 ml of boiling acetonitrile.

18.3 g of a compound are obtained, the melting point of which is 103° C. and the elemental analysis of which, calculated for $C_{13}H_{11}NO_3S+1$ mol of N-methylpyrrolidone, is:

|  | C | H | N | O | S |
|---|---|---|---|---|---|
| Theory | 59.98 | 5.59 | 7.77 | 17.76 | 8.90 |
| Found | 60.11 | 5.90 | 7.76 | 17.61 | 8.81 |

2nd step: Synthesis of 2-benzylthio-5-aminophenol.

The reduction is performed according to the procedure described in Example 1, step 2.

White crystals are obtained which, after recrystallization from boiling 95° strength ethanol, melt at 126° C. and the elemental analysis of which, calculated for $C_{13}H_{13}NOS$, is:

|  | C | H | N | O | S |
|---|---|---|---|---|---|
| Theory | 67.50 | 5.66 | 6.06 | 6.92 | 13.86 |
| Found | 67.56 | 5.66 | 5.99 | 7.06 | 13.97 |

PREPARATION EXAMPLE 5

Synthesis of 2-(β-hydroxyethylthio)-5-aminophenol 19.8 g of potassium hydroxide pellets are added to a solution of 35.1 g (0.45 mol) of thioethanol in 70 ml of N-methylpyrrolidone, and the mixture is stirred until dissolution is complete (exothermic—maintain the temperature at 45°–50° C.). 33.4 g (0.2 mol) of 4-nitro- 1,2-methylenedioxybenzene are then added portionwise in the course of 10 minutes.

After 1 hour of stirring at 50° C., the violet suspension is poured into 400 ml of ice-cold water.

This solution is acidified with 36% hydrochloric acid.

The orange-colored oil thus precipitated is separated after settling has taken place, washed several times with water and reduced directly according to the procedure described in Example 2, second step.

After purification by passage through a column of silica gel (eluent heptane/ethyl acetate), 2.5 g of white crystals (recrystallized from 1,2-dichloroethane) are obtained, the melting point of which is 79° C. and the elemental analysis of which, calculated for $C_8H_{11}NO_2S$, is:

|  | C | H | N | O | S |
|---|---|---|---|---|---|
| Theory | 51.87 | 5.99 | 7.56 | 17.27 | 17.31 |
| Found | 51.91 | 6.05 | 7.54 | 17.37 | 17.32 |

PREPARATION EXAMPLE 6

Synthesis of 2-(β-acetylaminoethylthio)-5-aminophenol

1st step: Synthesis of 2-(β-acetylaminoethylthio)-5-nitrophenol.

This compound is prepared according to the procedure described in Example 5, the reaction temperature being 70°–75° C.

Yellow crystals (recrystallized from 96° strength ethanol) are obtained, the melting point of which is 204° C. and the elemental analysis of which, calculated for $C_{10}H_{12}N_2O_4S$, is:

|  | C | H | N | O | S |
|---|---|---|---|---|---|
| Theory | 46.87 | 4.72 | 10.93 | 24.97 | 12.51 |
| Found | 46.78 | 4.80 | 10.86 | 24.74 | 12.36 |

2nd step: Synthesis of 2-(β-acetylaminoethylthio)-5-aminophenol

The reduction of the corresponding nitro derivative is performed according to the process of Example 1, step 2. White crystals (recrystallized from boiling 95° strength ethanol) are obtained, the melting point of which is 144° C. and the elemental analysis of which, calculated for $C_{10}H_{11}N_2O_2S+\frac{1}{4}$ mol of water, is:

|  | C | H | N | O | S |
|---|---|---|---|---|---|
| Theory | 52.04 | 6.33 | 12.14 | 15.60 | 13.89 |
| Found | 52.21 | 6.33 | 12.06 | 15.78 | 13.76 |

PREPARATION EXAMPLE 7

Synthesis of 2-methylthio-5-ureidophenol 10.9 g (0.07 mol) of the compound described in Example 1, step 2, are dissolved in a solution of 7 ml of 36% hydrochloric acid in 35 ml of water. A solution of 6.8 g of potassium cyanate in 21 ml of water is added in a single portion and at room temperature.

After the mixture has been stirred briskly for 2 hours, the crystallized precipitate formed is drained, made into a paste in water and recrystallized from boiling acetonitrile.

6.9 g of gray-violet crystals are obtained, the melting point of which is 136° C. and the elemental analysis of which, calculated for $C_8H_{10}N_2O_2S$, is:

|  | C | H | N | O | S |
|---|---|---|---|---|---|
| Theory | 48.47 | 5.08 | 14.13 | 16.14 | 16.17 |
| Found | 48.41 | 5.11 | 14.12 | 16.25 | 15.97 |

PREPARATION EXAMPLE 8

Synthesis of 2-methylthio-5-acetylaminophenol 10.9 g (0.07 mol) of the compound described in Example 1, step 2, 25 ml of dioxane and 7.5 ml of acetic anhydride are mixed.

After 30 minutes of heating on a boiling water bath, the reaction medium is cooled to 5° C. in an ice bath.

The crystallized precipitate is drained and recrystallized from boiling dimethoxyethane.

7.8 g of pink crystals are obtained, the melting point of which is 168° C. and the elemental analysis of which, calculated for $C_9H_{11}O_2NS$, is:

|  | C | H | N | O | S |
|---|---|---|---|---|---|
| Theory | 54.80 | 5.62 | 7.10 | 16.22 | 16.25 |
| Found | 54.89 | 5.62 | 7.18 | 16.40 | 16.29 |

PREPARATION EXAMPLE 9

Synthesis of 2-methylthio-5-carbethoxyaminophenol

A mixture of 10.9 g (0.07 mol) of the compound described in Example 1, step 2, 4.3 g of sodium carbonate and 35 ml of dioxane is heated on a boiling water bath. 7.6 ml of ethyl chloroformate are added dropwise and, after 1 hour of heating, the reaction medium is poured into 150 ml of ice-cold water.

The precipitate obtained, which is at first oily, crystallizes.

After draining, washing with water, and drying under vacuum in the presence of phosphoric anhydride, 11.3 g of light gray crystals (recrystallized from boiling benzene) are obtained, the melting point of which is 95° C. and the elemental analysis of which, calculated for $C_{10}H_{13}NO_3S$, is:

|  | C | H | N | O | S |
|---|---|---|---|---|---|
| Theory | 52.85 | 5.77 | 6.16 | 21.12 | 14.11 |
| Found | 52.85 | 5.78 | 6.24 | 21.08 | 14.11 |

Examples 1 to 8 illustrating the compositions appear in Table (I).

The pH of the compositions of Examples 1 to 4 after mixing weight for weight with a 20-volumes hydrogen peroxide solution the pH of which is adjusted to 3, and of Examples 5 to 8 after mixing weight for weight with a 20-volumes hydrogen peroxide solution, the pH of which is adjusted to 1.5, appears in Table II.

The mixture is applied to natural gray hair which is 90% white or to permanent-waved gray hair, for 30 minutes at room temperature. The hair is then rinsed, washed with shampoo, rinsed once again and then dried.

It is dyed the color shown at the bottom of Table II.

PREPARATION EXAMPLE 10

Preparation of 5-amino,2,4-bis(methylthio)phenol hydrochloride

1st step: Synthesis of 2,4-bis(methylthio)-5-nitrophenol 26.5 g (0.1 mol) of 5-nitro-6-(2,2,2-trifluoroethoxy)benzo[1,3]dioxole (RN 115132-98-4) are added portionwise to a suspension of sodium thiomethylate (0.3 mol) in 120 ml of dimethoxyethane at room temperature.

The reaction is exothermic.

At the end of the addition, the mixture is heated for half an hour at 60° C.

The reaction medium is poured into 1 liter of ice-cold water (solution) and acidified with acetic acid.

The crystallized precipitate is drained, made into a paste in water and dried under vacuum over phosphoric anhydride.

After recrystallization from ethyl acetate, orange-red crystals (7.8 g) are obtained, melting point 166° C., the elemental analysis of which, calculated for $C_8H_9NO_3S_2$, is:

|  | C | H | N | O | S |
|---|---|---|---|---|---|
| Theory | 41.54 | 3.92 | 6.06 | 20.75 | 27.73 |
| Found | 41.61 | 3.99 | 6.12 | 21.00 | 27.93 |

2nd step: reduction

A mixture of 0.8 g of ammonium chloride, 3.6 ml of water, 70 ml of 96° strength alcohol and 27 g of finely powdered zinc is heated to reflux of the alcohol.

The 2,4-bis(methylthio)-5-nitrophenol obtained in step 1 (6.9 g 0.03 mol) is added portionwise so as to maintain the reflux without heating.

The reaction is exothermic.

At the end of the addition, the heating to reflux is prolonged for 1 hour.

The reaction medium is filtered while boiling into 8 ml of an approximately 6N solution of hydrochloric acid in absolute alcohol. On cooling the filtrate, 5-amino- 2,4-bis(methylthio)phenol hydrochloride crystallizes.

The product is drained, washed with ethyl ether and dried under vacuum over potassium hydroxide.

4.0 g of white crystals are obtained, melting with decomposition at 182°–184° C., the elemental analysis of which, calculated for $C_8H_{12}ClNOS_2$, is:

|  | C | H | N | O | S | Cl |
|---|---|---|---|---|---|---|
| Theory | 40.41 | 5.09 | 5.89 | 6.73 | 26.97 | 14.91 |
| Found | 40.62 | 5.13 | 6.05 | 6.76 | 26.85 | 15.06 |

TABLE I

| Dye precursor | Ex 1 | Ex 2 | Ex 3 | Ex 4 | Ex 5 | Ex 6 | Ex 7 | Ex 8 |
|---|---|---|---|---|---|---|---|---|
| para-phenylene diamine | 0.32 |  | 0.32 |  |  |  |  | 0.10 |
| 2,6-dimethyl-p-phenylene diamine |  | 0.63 g |  | 0.63 g | 0.63 g | 0.63 g | 0.63 g |  |
| 2-(β-acetylaminoethylthio)-5-aminophenol | 0.68 |  |  |  |  |  |  |  |
| 2-methylthio- |  | 0.59 |  |  |  |  |  |  |

TABLE I-continued

| Dye precursor | Ex 1 | Ex 2 | Ex 3 | Ex 4 | Ex 5 | Ex 6 | Ex 7 | Ex 8 |
|---|---|---|---|---|---|---|---|---|
| 5-ureidophenol | | | | | | | | |
| 2-methylthio-5-acetyl-aminophenol | | | 0.59 g | | | | | |
| 2-ethylthio-5-aminophenol | | | | 0.51 g | | | | |
| 2-(β-hydroxetylthio)-5-aminophenol [sic] | | | | | 0.55 g | | | |
| 2-methylthio-5-carbethoxy-aminophenol | | | | | | 0.68 g | | |
| 2-benzylthio-5-aminophenol | | | | | | | 0.69 g | |
| 2-methylthio-5-aminophenol | | | | | | | | 0.15 g |
| Vehicle | Veh B | Veh B | Veh B | Veh B | Veh A | Veh A | Veh A | Veh A |
| pH | 9.5 | 9.1 | 9.4 | 9.1 | 9.1 | 9.1 | 9.1 | 9.5 |

TABLE II

| | Ex 1 | Ex 2 | Rx 3 | Ex 4 | Ex 5 | Ex 6 | Ex 7 | Ex 8 |
|---|---|---|---|---|---|---|---|---|
| pH mixture | 6.6 | 6.4 | 6.7 | 6.4 | 6.6 | 6.6 | 6.5 | 6.8 |
| Color natural gray hair | light chestnut brown | | | ashen dark blonde | | bluish ashen light blonde | | pearly ash-blonde |
| Color permanent-waved hair | | dark blonde | ashen dark chestnut brown | | light chestnut brown | | ashen natural blonde | |

EXAMPLE 9

| | |
|---|---|
| 5-Amino-2,4-bis(methylthio)phenol hydrochloride | 0.71 g |
| para-Phenylenediamine | 0.32 g |
| Vehicle A qs | 100 g | pH = 9.1

At the time of use, an equal weight of a 20-volumes hydrogen peroxide solution, the pH of which is adjusted to 1.5 with phosphoric acid, is added. The pH of the mixture is equal to 6.5.

The latter is applied to permanent-waved gray hair for 30 minutes at room temperature. After rinsing, washing with shampoo, rinsing and drying, the hair is dyed an ashen natural blonde.

VEHICLE A

| | |
|---|---|
| Polyglycerolated oleic [sic] alcohol containing 2 mol of glycerol | 4.0 g |
| Polyglycerolated oleic [sic] alcohol containing 4 mol of glycerol, containing 78% of AS | 5.69 g AS |
| Oleic acid | 3.0 |
| Oleic [sic] amine containing 2 mol of ethylene oxide, sold under the name ETHOMEEN O12 by the company AKZO | 7.0 g |
| Diethylaminopropyl laurylaminosuccinamate sodium salt containing 55% of AS | 3.0 g AS |
| Oleic [sic] alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl other | 9.0 g |
| Sodium metabisulfite in aqueous solution containing 35% of AS | 0.45 g AS |
| Ammonium acetate | 0.8 g |
| Antioxidant, sequestering agent | qs |
| Perfume, preservatives | qs |
| Monoethanolamine | qs pH 9.8 |
| Dyes | x g |
| Demineralized water | qs 100.0 g |

VEHICLE B

| | |
|---|---|
| Octyldodecanol sold under the name | 8.0 g |

-continued

| VEHICLE B | |
|---|---|
| EUTANOL D by the company HENKEL | |
| Oleic acid | 20.0 g |
| Monoethanolamine lauryl ether sulfate sold under the name SIPON LM 35 by the company HENKEL | 3.0 g |
| Ethyl alcohol | 10.0 g |
| Benzyl alcohol | 10.0 g |
| Cetyl/stearyl alcohol containing 33 mol of ethylene oxide, sold under the name SIMULSOL GS by the company SEPPIC | 2.4 g |
| Ethylene diaminetetraacetic acid | 0.2 g |
| Aqueous solution of polymer consisting of units: | 3.7 g AS |

$$\left[ -\underset{\underset{CH_3}{|}}{\overset{\overset{CH_3}{|}}{N^{\oplus}}}-(CH_2)_3-\underset{\underset{CH_3}{|}}{\overset{\overset{CH_3}{|}}{N^{\oplus}}}-(CH_2)_6- \right] \quad Cl^{\ominus} \quad Cl^{\ominus}$$

| Monoethanolamine | 7.5 g |
|---|---|
| Linoleic acid diethanolamide sold under the name COMPERLAN F by the company HENKEL | 8.0 g |
| Ammonia solution containing 20% of $NH_3$ | 10.2 g |
| Sodium metabisulfite in 35% aqueous solution | 1.3 g |
| Hydroquinone | 0.15 g |
| 1-Phenyl-3-methyl-5-pyrazolone | 0.2 g |
| Dyes | x g |
| Demineralized water qs | 100.0 g |

We claim:

1. Process for dyeing keratinous fibers, comprising applying to the keratinous fibers a composition suitable for dyeing keratinous fibers containing a compound corresponding to the formula:

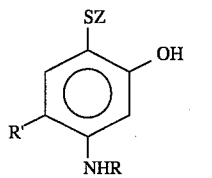

(I)

in which Z represents a $C_1$–$C_{18}$ alkyl radical, an aryl radical, an aralkyl radical in which the alkyl radical contains 1 to 6 carbon atoms, a $C_1$–$C_6$ monohydroxyalkyl radical, a $C_1$–$C_6$ polyhydroxyalkyl radical, an aminoalkyl radical of formula:

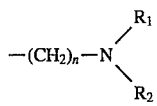

in which n is an integer between 1 and 6 inclusive, $R_1$ and $R_2$, which may be identical or different, represent a hydrogen atom, a $C_1$–$C_4$-alkyl, $C_1$–$C_4$ hydroxyalkyl, or $C_2$–$C_6$ or acyl radical;

R represents a hydrogen atom, a $C_1$–$C_6$ alkyl radical, a $C_1$–$C_6$ monohydroxyalkyl, $C_2$–$C_6$ polyhydroxyalkyl, monocarbamyl ($C_1$–$C_6$ alkyl), dicarbamyl($C_1$–$C_6$ alkyl), $C_1$–$C_6$ aminoalkyl, $C_1$–$C_6$ acyl, $C_2$–$C_6$ carbalkoxy, carbamyl or mono ($C_1$–$C_6$ alkyl)carbamyl radical, R' represents a hydrogen atom, a $C_1$–$C_4$ alkyl, $C_1$–$C_4$ thioalkyl or $C_1$–$C_4$ alkoxy radical, or the corresponding salts with an acid, the compound of formula (I) being present in proportions of between 0.05 and 3.5% by weight relative to the total weight of the composition.

2. Process according to claim 1, wherein, in the compound of formula (I), Z denotes methyl, ethyl, propyl, or butyl phenyl; benzyl; —$CH_2$—$CH_2OH$, —$CH_2CHOH$—$CH_2$—OH, —$CH_2CHOH$—$CH_3$, —$CH_2$—$CH_2$—$NH_2$,

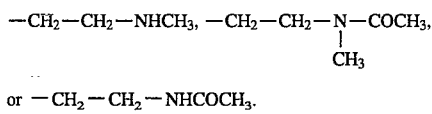

or —$CH_2$—$CH_2$—$NHCOCH_3$.

3. Process according to claim 1, wherein in the compound of formula (I), the group R is formyl, acetyl or propionyl.

4. Process according to claim 1, wherein the compound is:
—2-methylthio-5-aminophenol,
—2-ethylthio-5-aminophenol,
—2-butylthio-5-aminophenol,
—2-benzylthio-5-aminophenol,
—2-(β-hydroxyethylthio)-5-aminophenol,
—2-(β-acetylaminoethylthio)-5-aminophenol,
—2-methylthio-5-ureidophenol,
—2-methylthio-5-acetylaminophenol,
—2-methylthio-5-(carbethoxyamino)phenol,
—2,4-bis(methylthio)-5-aminophenol,
—2 -(4'-amino-2'-hydroxyphenyl)thio-5-aminophenol,
—2 -(4'-nitrophenyl)thio-5-aminophenol,
—2 -(2'-aminophenyl)thio-5-aminophenol.

5. Process according to claim 1, wherein the compound of formula (I) is applied to keratinous fibers as a coupler for the oxidation dyeing of keratinous fibers in combination with para oxidation dye precursors, ortho oxidation dye precursors, or mixtures thereof.

6. Dyeing composition for keratinous fibers, comprising in a medium suitable for the dyeing of these fibers, at least one para dye precursor, ortho dye precursor, or mixtures thereof, and at least, as a coupler, one sulfur-containing meta-aminophenol corresponding to the formula (I)

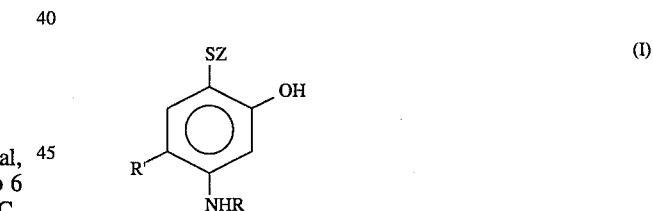

(I)

in which Z represents a $C_1$–$C_{18}$ alkyl radical, an aryl radical, an aralkyl radical in which the alkyl radical contains 1 to 6 carbon atoms, a $C_1$–$C_6$ monohydroxyalkyl radical, a $C_2$–$C_6$ polyhydroxyalkyl radical, an aminoalkyl radical of formula:

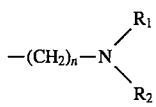

in which q is an integer between 1 and 6 inclusive, $R_1$ and $R_2$, which may be identical or different, represent a hydrogen atom, a $C_1$–$C_4$-alkyl, $C_1$–$C_4$ hydroxyalkyl, or $C_2$–$C_6$ acyl radical;

R represents a hydrogen atom, a $C_1$–$C_6$ alkyl radical, a $C_1$–$C_6$ monohydroxyalkyl, $C_2$–$C_6$ polyhydroxyalkyl, monocarbamyl ($C_1$–$C_6$ alkyl), dicarbamyl ($C_1$–$C_6$ alkyl), $C_1$–$C_6$ aminoalkyl, $C_1$–$C_6$ acyl, $C_2$–$C_6$ carbalkoxy, carbamyl or mono($C_1$–$C_6$ alkyl)carbamyl radical, R' represents a hydrogen atom, a $C_1-C_4$ alkyl, $C_1-C_4$ thioalkyl or $C_1-C_4$ alkoxy radical, or the corresponding salts with an acid, the compound of formula (I) being present in proportions of between 0.05 and 3.5% by weight relative to the total weight of the composition.

7. Composition according to claim 6, wherein the compound of formula (I) is:
—2-methylthio-5-aminophenol,
—2-ethylthio-5-aminophenol,
—2-butylthio-5-aminophenol,
—2-benzylthio-5-aminophenol,
—2-($\beta$-hydroxyethylthio)-5-aminophenol,
—2-($\beta$-acetylaminoethylthio)-5-aminophenol,
—2-methylthio-5-ureidophenol,
—2-methylthio-5-acetylaminophenol,
—2-methylthio-5-carbethoxyaminophenol,
—2,4-bis(methylthio)-5-aminophenol,
—2-(4'-amino-2'-hydroxyphenyl)thio-5-aminophenol,
—2-(4'-nitrophenyl)thio-5-aminophenol,
—2-(2'-aminophenyl)thio-5-aminophenol.

8. Composition according to claim 6 wherein the oxidation dye precursors are para-phenylene diamines, para-aminophenols, heterocyclic para precursors derived from pyridine or from pyrimidine, pyrazole derivatives, ortho-aminophenols, or bis(phenyl)alkylenediamines.

9. Composition according to claim 8, wherein the paraphenylenediamines are compounds corresponding to the formula:

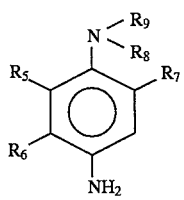

(VI)

in which:

$R_5$, $R_6$, $R_7$, which may be identical or different, represent a hydrogen or halogen atom, an alkyl radical, an alkoxy radical, a carboxyl, sulfo, or $C_1-C_4$ hydroxyalkyl radical;

$R_8$ and $R_9$, which may be identical or different, represent a hydrogen atom, an alkyl, hydroxyalkyl, alkoxyalkyl, carbamylalkyl, mesylaminoalkyl, acetylaminoalkyl, ureidoalkyl, carbalkoxyaminoalkyl, sulfoalkyl, piperidinoalkyl, or morpholinoalkyl radical, a phenyl radical optionally substituted at the para position with an amino group; or alternatively $R_8$ and $R_9$, together with the nitrogen atom to which they are linked, form a piperidino or morpholino heterocycle, with the proviso that $R_5$ or $R_7$ represent a hydrogen atom when $R_8$ and $R_9$ do not represent a hydrogen atom, or the salts of the compounds.

10. Composition according to claim 9, wherein the paraphenylenediamines are paraphenylenediamine, p-toluylenediamine, chloro-paraphenylenediamine, 2,3-dimethyl-paraphenylenediamine, methoxy-para-phenylenediamine, 2,6-dimethyl-para-phenylenediamine, 2,6-diethyl-paraphenylenediamine, 2,5-dimethyl-para-phenylenediamine, 2-methyl-5-methoxy-paraphenylenediamine, 2,6-dimethyl-5-methoxy-paraphenylenediamine, N,N-dimethyl-para-phenylenediamine, N,N-diethyl-para-phenylenediamine, N,N-dipropyl-paraphenylenediamine, 3-methyl-4-amino-N,N-diethylaniline, N,N-di($\beta$-hydroxyethyl)-para-phenylenediamine, 3-methyl-4-amino-N,N-di($\beta$-hydroxyethyl)aniline, 3-chloro-4-amino-N,N-di($\beta$-hydroxyethyl)aniline, 4-amino-N,N-(ethyl,carbamylmethyl)aniline, 3-methyl-4-amino-N,N-(ethyl,carbamylmethyl)aniline, 4-amino-N,N-(ethyl,$\beta$-piperidinoethyl)aniline, 3-methyl-4-amino-N,N-(ethyl,$\beta$-piperidinoethyl)aniline, 4-amino-N,N-(ethyl,$\beta$-morpholinoethyl)aniline, 3-methyl-4-amino-N,N-(ethyl,$\beta$-morpholinoethyl)aniline, 4-amino-N,N-(ethyl,$\beta$-acetylaminoethyl)aniline, 4-amino-N-($\beta$-methoxyethyl)aniline, 3-methyl-4-amino-N,N-(ethyl,$\beta$-acetylaminoethyl)aniline, 4-amino-N,N-(ethyl,$\beta$-mesylaminoethyl)aniline, 3-methyl-4-amino-N,N-(ethyl,$\beta$-mesylaminoethyl)aniline, 4-amino-N,N-(ethyl,$\beta$ -sulfoethyl) aniline, 3-methyl-4-amino-N,N-(ethyl,$\beta$ -sulfoethyl) aniline, N-[(4'-amino)phenyl]morpholine, N-[(4'-amino)phenyl]piperidine, 2-hydroxyethyl-p-phenylenediamine, fluoro-para-phenylenediamine, carboxy-para-phenylenediamine, sulfo-paraphenylenediamine, 2-isopropyl-para-phenylenediamine, 2-n-propyl-para-phenylenediamine, hydroxy-2-n-propyl-paraphenylenediamine, 2-hydroxymethyl-para-phenylenediamine, N,N-dimethyl-3-methyl-p-phenylenediamine, N,N-(ethyl,$\beta$-hydroxyethyl)-p-phenylenediamine, N-(dihydroxypropyl)-p-phenylenediamine, N'-4'-aminophenyl-p-phenylenediamine or N-phenyl-p-phenylenediamine.

11. Composition according to claim 8, wherein the para-aminophenols are chosen from p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2-hydroxymethyl-4-aminophenol, 2-($\beta$-hydroxyethyl)-4-aminophenol, 2-methoxy-4-aminophenol, 3-methoxy-4-aminophenol, 3-($\beta$-hydroxyethoxy)-4-aminophenol, 2-aminomethyl- 4-aminophenyl, 2-$\beta$-hydroxyethylaminomethyl-4-aminophenol [sic], 2-methoxymethyl-4-aminophenol, 2-ethoxymethyl-4-aminophenol, or 2-($\beta$-hydroxyethoxymethyl)-4-aminophenol.

12. Composition according to claim 8, wherein the ortho-aminophenols are 1-amino-2-hydroxybenzene, 6-methyl-1-hydroxy-2-aminobenzene, 4-methyl-1-amino-2-hydroxybenzene, or 4-acetylamino-1-amino- 2-hydroxybenzene.

13. Composition according to claim 8, wherein the bis(phenyl)alkylenediamines correspond to the formula:

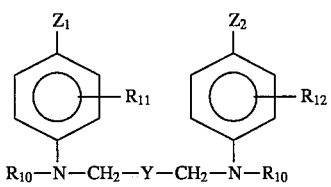

(VII)

in which:

$Z_1$ and $Z_2$, which may be identical or different, represent hydroxyl groups or $NHR_{13}$ groups, where $R_{13}$ denotes a hydrogen atom or a lower alkyl radical;

$R_{11}$ and $R_{12}$, which may be identical or different, represent hydrogen atoms or halogen atoms or alkyl groups;

$R_{10}$ represents a hydrogen atom, an alkyl, a hydroxyalkyl group or an aminoalkyl group in which the amino residue may be substituted;

Y represents a radical selected from the group consisting of the following radicals:

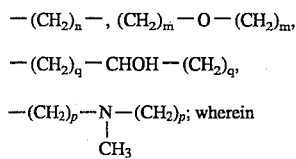

n is an integer between 0 and 8 and m, q and p are integers between 0 and 4, or its addition salts with acids.

14. Composition according to claim 13, wherein the bis(phenyl)alkylenediamines are N,N'-bis(β-hydroxyethyl)-N,Nβ-bis(4β-aminophenyl)-1,3-diamino- 2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis( 4-aminophenyl ) tetramethylenediamine, N,N'-bis(4-methylaminophenyl)tetramethylenediamine, N,N'-bis(ethyl) N,N' -bis(4'-amino-3'-methylphenyl)ethylenediamine.

15. Composition according to claim 6 wherein the compositions contain, in addition to the coupler of formula (I) as defined above, additional couplers which are meta-diphenols, meta-aminophenols, meta-phenylenediamines, meta-acylaminophenols, meta-ureidophenols, meta-carbalkoxyaminophenols, α-naphthol, indole derivatives, couplers possessing an active methylene group, or pyrazolones.

16. Composition according to claim 15, wherein the additional couplers are 2,4-dihydroxyphenoxyethanol, 2,4-dihydroxyanisole, meta-aminophenol, resorcinol monomethyl ether, resorcinol, 2-methylresorcinol, 2-methyl-5-aminophenol, 2-methyl-5-N-(β-hydroxyethyl)aminophenol, 2-methyl-5-N-(β-mesylaminoethyl)aminophenol, 2,6-dimethyl-3-aminophenol, 6-hydroxybenzomorpholine, 2,4-diaminoanisole, 2,4-diaminophenoxyethanol, 6-aminobenzomorpholine, [2-N-(β-hydroxyethyl)amino- 4-amino]phenoxyethanol, 2-amino-4-N-(β-hydroxyethyl)aminoanisole, (2,4-diamino)phenyl β,γ-dihydroxypropyl ether, 2,4-diaminophenoxyethylamine, 1,3-dimethoxy-2,4-diaminobenzene, 1,3,5-trimethoxy-2,4-diaminobenzene, 1-amino-3,4-methylenedioxybenzene, 1-hydroxy-3,4-methylenedioxybenzene, 2-chloro-6-methyl-3-aminophenol, 2-methyl-3-aminophenol, 2-chlororesorcinol, 6-methoxy-3-hydroxyethylaminoaniline, 1-ethoxy-2-bis-(β -hydroxyethyl)amino-4-aminobenzene, 3-diethylaminophenol, 1,3-dihydroxy-2-methylbenzene, 1-hydroxy-2,4-dichloro- 3-aminobenzene, 4,6-hydroxyethoxy-1,3-diaminobenzene, 4-methyl-6-ethoxy-1,3-diaminobenzene, 4-chloro- 6-methyl-3-aminophenol, 6-chloro-3-trifluoroethylaminophenol, and their salts.

17. Composition according to claim 6, wherein the dyeing composition contains direct dyes which are azo dyes, anthraquinone dyes or nitro derivatives of the benzene series.

18. Composition according to claim 6, wherein the oxidation dye precursors and the couplers are present in the dyeing compositions in proportions of between 0.3 and 7% by weight relative to the total weight of the composition.

19. Composition according to claim 6, wherein the appropriate medium for the dyeing is aqueous, and its pH is between 4 and 11.

20. Process for dyeing keratinous fibers, comprising applying to the keratinous fibers a composition having a pH below 8 obtained by mixing the dyeing composition defined in claim 6 with an oxidizing solution used in sufficient amounts to develop a coloration.

21. Process according to claim 20, wherein the pH of the composition applied to the keratinous fibers is between 3.5 and 7.

* * * * *